United States Patent [19]
Malczewski et al.

[11] Patent Number: 5,537,879
[45] Date of Patent: Jul. 23, 1996

[54] PARTICLE SAMPLING SYSTEM FOR GAS SUPPLY SYSTEM

[75] Inventors: Mark L. Malczewski, North Tonawanda; Arthur E. Holmer, Lewiston; Hollis C. Demmin, Tonawanda, all of N.Y.

[73] Assignee: Praxair Technology, Inc., Danbury, Conn.

[21] Appl. No.: 510,285

[22] Filed: Aug. 2, 1995

[51] Int. Cl.$^6$ ..................................... G01N 1/20
[52] U.S. Cl. .............. 73/863.61; 73/28.01; 73/863.58
[58] Field of Search ............ 73/863.58, 863.61, 73/28.01, 863.81

[56] References Cited

U.S. PATENT DOCUMENTS

| | | | |
|---|---|---|---|
| 4,522,218 | 6/1985 | Konak | 73/863.61 X |
| 4,527,435 | 7/1985 | Hall et al. | 73/863.61 X |
| 4,566,342 | 1/1986 | Kurz | 73/863.58 X |
| 4,998,954 | 3/1991 | Burr | 73/863.58 |
| 5,052,425 | 10/1991 | Hohenberg et al. | 73/863.58 X |
| 5,115,687 | 5/1992 | Clingman, Jr. et al. | 73/863.61 |
| 5,231,865 | 8/1993 | McDermott et al. | 73/28.04 |
| 5,279,146 | 1/1994 | Asano et al. | 73/28.01 X |
| 5,417,105 | 5/1995 | Martinez et al. | 73/863.58 X |
| 5,460,054 | 10/1995 | Tran | 73/863.61 |

OTHER PUBLICATIONS

*Microcontamination*, Mar. 1992, "Providing Next–Generation Particle Measurement and Control for Ultra–High–Purity Distribution Systems" J. D. Borkman, W. R. Couch and M. L. Malczewski, 7 pages.
Particle Measuring Systems Inc., Data Sheet, High Pressure Gas Probes 2 pages published by Jul. 1995.

*Primary Examiner*—Thomas P. Noland
*Attorney, Agent, or Firm*—Stanley Ktorides

[57] ABSTRACT

A particle sampling system which includes a flow restrictor positioned in a conduit between a vent and an analyzer probe and restricts flow in the conduit to maintain an overpressure of sample gas at the counter probe which, in turn, forces the gas sample into the particle analyzer. The system further includes a reservoir for holding a working fluid usable with a particle analyzer and a pressurized gas source which is used to pressurize the reservoir to enable supply of the working fluid against the pressure of the gas analysis sample and to provide a purge gas for the analyzer.

10 Claims, 2 Drawing Sheets

PARTICLE SAMPLING SYSTEM FOR GAS SUPPLY SYSTEM

FIELD OF THE INVENTION

This invention relates to particle sampling systems usable with gas streams and, more specifically, to a particle sampling system usable with reactive gases.

BACKGROUND OF THE INVENTION

Ultra-high purity gases are widely used in the semiconductor industry and must meet stringent particulate content specifications. In order to assure that a gas supply meets such specifications, a sampling system is connected to the gas supply and provides samples of the gas to a particle analyzer. The sampling system analyzer must generally perform the following functions:

(1) provide a sample from the pressurized process gas stream that is isokinetic with the gas stream;

(2) reduce the pressure of the process gas sample to atmospheric;

(3) transport the atmospheric level sample to the particle analyzer; and (4) vent analyzed gases safely from the system.

As used herein, the term "isokinetic" means that gas entering the sampling system exhibits equal velocity and kinetic energy to the gas flow in the pressurized process gas stream. Such isokinetic sampling is generally achieved by assuring that the probe which samples the gas is oriented along the flow path and is positioned parallel to the gas flow from which the sample is taken. The sample gas flow is adjusted through, for example, use of a restrictor.

Recent advances in particle analyzers have extended their use to process gases other than air or nitrogen. For instance, condensation nucleus particle counters (CNC's) have been introduced that are usable in oxygen and hydrogen gas streams. Such a CNC particle counter (i.e. the CPC 7651) is available from TSI Inc., 500 Cardigan Rd., St. Paul, Minn. 55164. CNC type instruments require that the gas sample be supplied at slightly above atmospheric pressure to force the sample through the counter; that a source of purge gas be provided so as to enable purging from the CNC of the reactive gas; and that a liquid fill system be provided which supplies the instrument with a working fluid. Such a liquid fill system requires slight pressurization to overcome the sample gas pressurization level.

Borkman et al. in "Providing Next-Generation Particle Measurement and Control For Ultra-High-Purity Gas Distribution Systems" Microcontamination, March 1992, disclose a gas sampling system that is usable with ultra high purity gas sources. Borkman et al. employ a pitot probe positioned iso-axially in the process gas line. Typical process gas pressures are on the order of 80 to 120 psig. The flow withdrawn by the pitot probe and its diameter are adjusted to allow iso-kinetic sampling of the process gas from the pipeline. The pitot probe is connected to a pressure reduction device which reduces the sampled gas to atmospheric pressure. Details of the pressure reduction device are disclosed in U.S. Pat. No. 4,998,954 to Burr, the disclosure of which is incorporated herein by reference. Briefly stated, Burr describes a retractable iso-kinetic probe that is insertable into the gas flow line through an aligned guide tube. The probe provides an iso-kinetic gas sample to a converging/diverging nozzle where the pressure of the gas is reduced to atmospheric by a controlled shock wave.

The Burr probe and pressure reduction assembly neither loses particles in the sample stream nor releases additional particles to it. After pressure reduction, the sampled gas is transported to a sample horn where a second pitot probe draws the actual sample that is to be analyzed by the particle counter. Again, the second pitot probe diameter is adjusted to provide iso-kinetic sampling of the approximately atmospheric level gas sample.

At least two types of counters have been employed in prior art gas sampling systems. The first type comprises laser-based particle counters which count and size individual particles directly. Such a counter may be used directly at process gas line pressure and also may be used with hydrogen and oxygen directly. The limitation of laser-based particle counters is that the lowest detectable particle size is on the order of 0.05 to 0.1 microns in diameter. A second type of particle counter is the CNC type, described above. Until recently, CNC type counters have been restricted to use at atmospheric pressure and in air or with an inert gas. CNC counters, however, offer detection limits of less than 0.01 microns and thus, in theory, they can provide lower detection limits by a factor of 5 to 10 over laser-based counters. Present CNC designs employ an internal pump, or a critical orifice with an external sample pump, to assure a flow of sample gas to the CNC. Such pumps render the CNC type counter unusable with hydrogen or oxygen gas because the pump is a potential ignition source.

U.S. Pat. No. 5,231,865 to McDermott et al. discloses a method for use of a CNC counter in a hydrogen gas flow. McDermott et al. utilize a dilution and diffusion apparatus positioned ahead of the CNC. Their approach is to convert the processed hydrogen sample stream from pure hydrogen, which the particle counter cannot handle, to a mixture of hydrogen and predominately nitrogen, which can be handled safely by the instrument.

Although the dilution method disclosed by McDermott et al. is useful for sampling hydrogen, it has a number of disadvantages. First, the diffusion/dilution apparatus is mechanically complex and gas flow rates and flow patterns must be carefully maintained. Next, the apparatus places another device in the sample flow path between the sample point and the CNC counter, which device may itself generate particles resulting in an erroneously high particle concentration reading by the CNC. Furthermore, the transport losses of particles in the device may lead to an erroneously low particle count. Lastly, because the CNC is used in a mixture of hydrogen and nitrogen, there is a question whether or not the particle counter is performing as accurately in the hydrogen/nitrogen mixture as it does in a pure hydrogen flow.

Accordingly, it is an object of this invention to provide a particle sampling system with means for providing a sample gas at an overpressure to a particle analyzer.

It is another object of this invention to provide a particle sampling system wherein a means for providing the sample gas at an overpressure to a particle analyzer provides sample gas which is representative of the pressurized gas.

It is a further object of this invention to provide a particle sampling system which is usable with reactive gases.

It is yet another object of this invention to provide a particle sampling system wherein provision is made to provide a working fluid to the particle analyzer when the sample gas is supplied at a slight overpressure.

SUMMARY OF THE INVENTION

The particle sampling system of the invention obtains a gas sample from a pressurized gas feed stream and determines characteristics of entrained particulate matter. The system includes a probe in communication with the pressurized feed stream for providing a gas sample stream that is iso-kinetic with the pressurized gas feed stream and provides the gas sample at approximately atmospheric pressure. A conduit couples the probe to a vent. A particle analyzer includes an analyzer probe that communicates with the conduit and provides an analysis sample to the analyzer. A flow restrictor is positioned in the conduit between the vent and the analyzer probe and restricts flow in the conduit so as to maintain a slight overpressure of sample gas at the counter probe which, in turn, forces the gas sample into the particle analyzer. The system further includes a reservoir for holding a working fluid usable with the particle analyzer and a pressurized gas source which is used to pressurize the reservoir to enable supply of the working fluid against the pressure of the gas analysis sample and also to provide a purge gas for the analyzer.

DETAILED DESCRIPTION OF THE INVENTION

Figure 1:
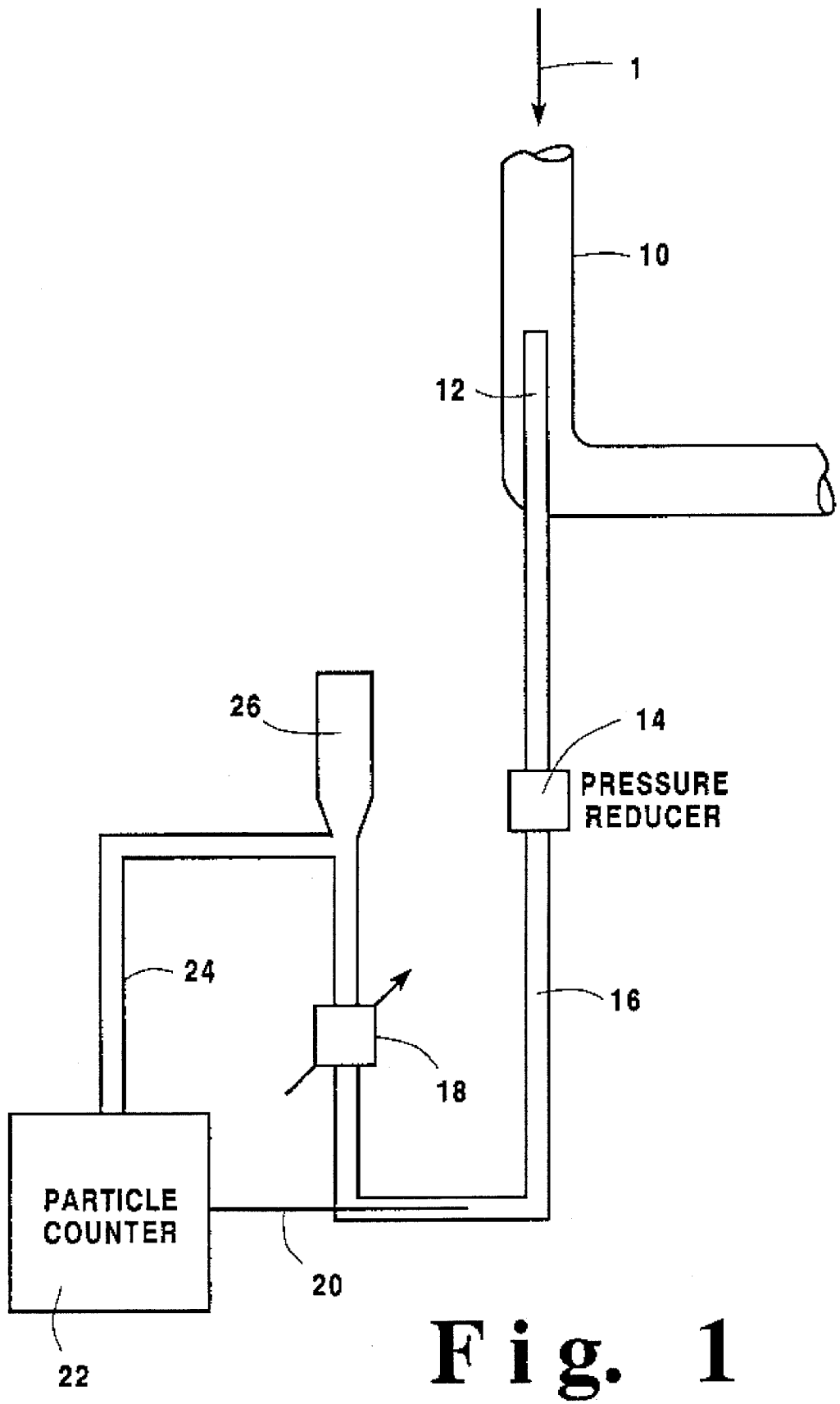
FIG. 1 is a schematic showing a preferred embodiment of the invention.

Referring to FIG. 1, a process gas pipe 10 carries product gas 1 at an elevated pressure, e.g. in the range of 50 to 150 pounds per square inch gauge (psig). The product gas may be any suitable gas or gas mixture, such as nitrogen, oxygen or argon gas. The invention is particularly advantageous when the product gas is a reactive gas, such as hydrogen or oxygen. A gas probe 12 is positioned in gas pipe 10 and provides an iso-kinetic flow of a sample of the product gas to a pressure reducer 14. Gas probe 12 and pressure reducer 14 are preferably configured in the manner taught by Burr in U.S. Pat. No. 4,998,954; however, it is to be understood that other devices which provide an iso-kinetic flow of sample gas from pipe 10 are also acceptable. Pressure reducer 14, in the means taught by Burr, reduces the sample gas pressure to approximately atmospheric.

The sample gas flow passes via a conduit 16 to a flow restrictor 18 that is preferably adjustable. Within conduit 16, a particle counter probe 20 provides a flow of sample gas to particle counter 22 for analysis. Particle counter 22 exhausts the sample gas via conduit 24 to a vent 26. The outflow from restrictor 18 also passes through vent 26 and is exhausted. Restrictor 18 is a back pressure regulator which preferably holds from 0 to 5 psig pressure in conduit 16. The adjustability feature of restrictor 18 enables a range of pressures to be established in conduit 16 and, more particularly, at the entrance to particle counter probe 20. Variable restrictor 18 is positioned downstream from counter probe 20. At such a location, variable restrictor 18 neither adds particles to nor removes particles from the sample gas flow that is detected by counter probe 20. Furthermore, restrictor 18 includes no moving parts which might serve as possible ignition points when particulate matter in a reactive gas stream is being sampled.

Gas probe 12 and pressure reducer 14 are sized so that, preferably, approximately 35 standard cubic feet per hour (SCFH) is drawn from the process gas flow in pipe 10. Proper choice of the inner diameter of probe 12 ensures that this flow rate yields iso-kinetic sampling. Preferably ¼ inch electropolished stainless steel (EP/SS) tubing is used to transport the sample gas from pressure reducer 14 to the location of particle counter 22. The distance between pressure reducer 14 and counter probe 20 is preferably less than 25 ft, and interconnecting conduit 16 exhibits a minimum number of bends. Any bends in the tube are made using ¼ inch EP/SS elbows which are orbitally butt welded to the tubing.

Near particle counter 22, conduit 16 transitions into a ½ inch EP/SS tube via a smooth transition. A run of the ½ inch EP/SS tubing is used as a sample horn, is mounted horizontally and is positioned for a straight run to smooth out the flow profile immediately ahead of counter probe 20. In practice, a sample horn length of 12 to 18 inches is preferred and provides a laminar velocity profile to the sample gas. Counter probe 20 is made from ¼ inch EP/SS tubing and inserts into the ½ inch EP/SS sample horn via compression fittings.

Restrictor 18 enables a back pressure of approximately 0.5 to 7 psig and preferably from 2 to 4 psig for the sample gas. The output exhaust from particle counter 22 is via conduit 24 which rejoins vent 26 downstream from restrictor 18. This maintains the pressure drop across particle counter 22 and allows the sample gas to flow through the instrument at the proper flow rate without the use of a sample pump. Particle counter 22 is thus maintained at a positive pressure relative to the atmosphere. To reiterate, neither particle additions nor particle losses within restrictor 18 affect the operation of the invention became the sample gas is taken into particle counter 22 before the gas flow reaches restrictor 18.

Figure 2:
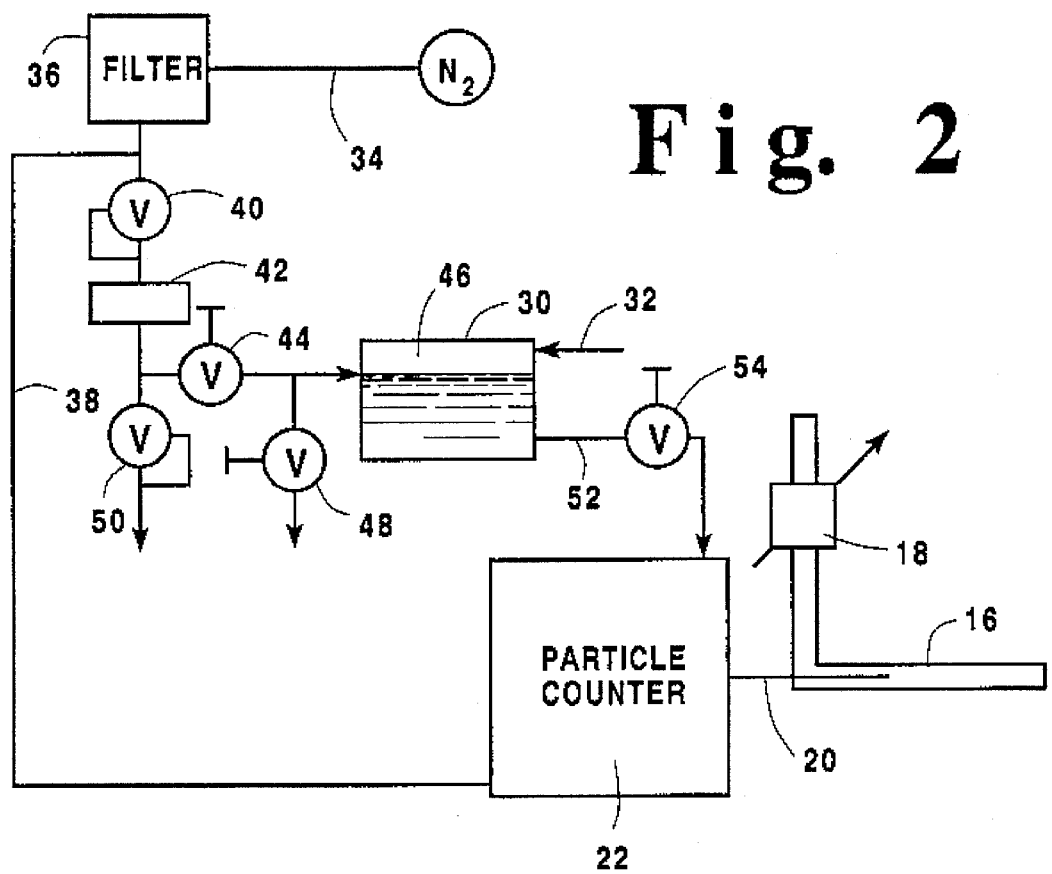
FIG. 2 is a schematic showing a preferred system for providing working fluid to a particle counter employed in the system of FIG. 1.

Turning now to FIG. 2, details of the pressurized liquid fill system (not shown in FIG. 1) for particle counter 22 will be described. As noted above, the slight pressurization of the sample gas at counter probe 20 enables efficient handling of a sample gas in counter 22 and is particularly important when counter 22 is employed with a reactive gas such as hydrogen or oxygen. When particle counter 22 is a CNC type, it requires a periodic addition of a working fluid to maintain its ability to count particles. The fluid is generally either n-butyl alcohol or a perfluorinated hydrocarbon. In the prior art, this liquid has been gravity fed to counter 22 when liquid is called for by internal control circuitry within particle counter 22. However, as a result of the slight pressurization of sample gas being fed into particle counter 22, a gravity feed cannot assure a proper flow of working fluid.

In FIG. 2, the working fluid is maintained in a reservoir 30 and is supplied thereto via a fill tube 32. Nitrogen, at approximately 80 to 120 psig, is fed via tube 34 to a filter 36. From there, the nitrogen is fed via a T-junction to a tube 38 and from there directly to particle counter 22. The nitrogen flow from tube 38 is employed as a purge gas and is selectively enabled by internal controls within particle counter 22. Nitrogen flow from filter 36 is also applied, via a pressure regulator 40, to a flow restrictor 42. Nitrogen from flow restrictor 42 passes through a valve 44 to head space 46 within reservoir 30. A vent valve 48 is employed to vent head space 46 when reservoir 30 is being filled via fill tube 32. A safety valve 50 is connected to the output flow from flow restrictor 42 and communicates with vent 26.

Pressure regulator 40 has a preferred working range of from 0 to 15 psig and has a typical setting of 4 to 5 psig. This enables the nitrogen flow into head space 46 to pressurize the liquid within reservoir 30 to a level of 4 to 5 psig. Working fluid is passed out from reservoir 30 via conduit 52 and valve 54 to particle counter 22.

Flow restrictor 42 and safety valve 50 are employed to provide a safety system in the event pressure regulator 40 fails. Such a failure could cause the entire contents of reservoir 30 to be forced into particle counter 22. Safety valve 50 is set at a pressure that is well above the typical working pressure within head space 46 (4 to 5 psig) and is preferably set at 10 psig. Flow restrictor 42 restricts the maximum flow from pressure regulator 40 in the event of a failure. Thus, even at full line pressure, the amount of gas that can be provided through flow restrictor 42 is small enough that it can be safely exhausted by safety valve 50.

When reservoir 30 is refilled, valve 54 is closed to prevent back flow of sample gas into reservoir 30 during the refill operation. Valve 44 is also closed to isolate the gas supply line. Valve 48 is then opened, thereby depressurizing head space 46 and allowing it to be refilled through tube 32.

The pressurized liquid fill system shown in FIG. 2 offers a number of advantages. Head space 46 in reservoir 30 is always filled with inert gas. Working fluid supply from reservoir 30 can be used for multiple particle counters, with each counter operating at a different inlet pressure. The pressure in head space 46 is independent of the inlet pressure of any counter which uses reservoir 30, and reservoir 30 may be positioned anywhere because gravity feed is not used to force a flow of the working fluid into particle counter 22. Moreover, the particle counters can be easily taken off-line and the reservoir refilled.

Figure 3:
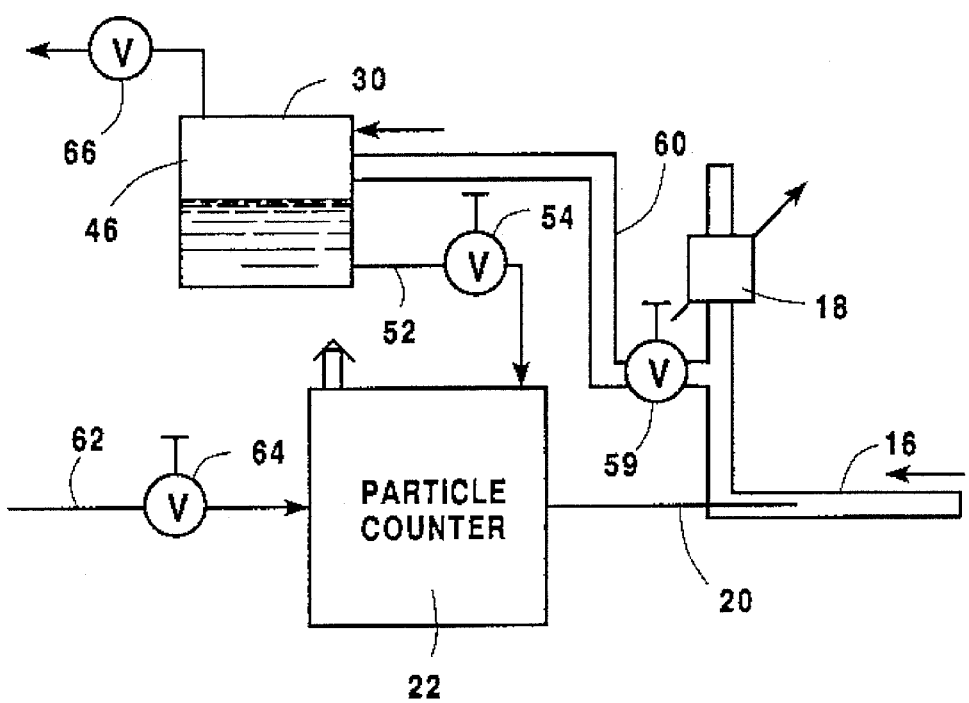
FIG. 3 is a second embodiment of a system for providing a working fluid to the particle counter of FIG. 1.

In FIG. 3, a further embodiment of a pressurized liquid fill system is illustrated that is not as preferred as the embodiment shown in FIG. 2. In FIG. 3, the pressurizing source for reservoir head space 46 is via valve 59 and tube 60 which is positioned to communicate with conduit 16 upstream from variable restrictor 18. As a result, head space 46 is pressurized at the same level as the sample gas pressure input to counter probe 20. The working liquid is then forced into particle counter 22 via conduit 52 and valve 54 by a gravity head. The nitrogen purge gas is fed from a separate supply line 62 via valve 64 to particle counter 22. A valve 66 enables venting of head space 46.

While the working fluid supply shown in FIG. 3 is simpler than that of FIG. 2, it requires that head space 46 be pressurized with the sample gas. Typically, this arrangement is utilized with inert process gases such as nitrogen or argon, etc. Further, if multiple counters share the output from reservoir 30, the head space pressure must be generated from the highest inlet pressure particle counter. This may result in excessive fill rates into lower pressure counters. This problem, of course, is not present when only a single particle counter is connected to reservoir 30.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A system for obtaining a gas sample from a gas feed stream and determining characteristics of particulate matter entrained therein, said system comprising:

probe means in communication with said pressurized gas feed stream for providing a gas sample that is iso-kinetic with said gas feed stream, and for providing said gas sample at an output above atmospheric pressure;

conduit means for coupling said probe means to a vent;

a particle analyzer;

an analyzer probe in communication with said conduit means for providing an analysis sample of said gas sample to said particle analyzer; and flow restriction means positioned in said conduit means between said vent and said analyzer probe, for restricting flow of said gas sample in said conduit means and for maintaining an overpressure of said gas sample at said analyzer probe so as to force at least a portion of said gas sample into said particle analyzer.

2. The system as recited in claim 1, wherein said analyzer probe is positioned in said conduit means and provides an iso-kinetic flow of sample gas to said particle analyzer.

3. The system as recited in claim 1, wherein said flow restriction means is adjustable and enables an alteration of said overpressure.

4. The system as recited in claim 1, further comprising:

a sample gas exhaust conduit connected from said particle analyzer to said vent at a position that is downstream from said flow restriction means.

5. The system as recited in claim 1 further comprising:

a reservoir for holding a working fluid;

a pressurized gas source coupled to said particle counter;

conduit means connecting said reservoir to said particle counter; and pressure reduction means coupled between said pressurized gas source and said reservoir, for feeding said pressurized gas at a reduced pressure to said reservoir, said reduced pressure being at a level that is not less than said overpressure of a gas sample within said particle analyzer.

6. The system as recited in claim 5 further comprising:

safety valve means having an output coupled to a vent and having inputs from said pressure reduction means and said reservoir, and operative upon a pressure of said pressurized gas exceeding a safety level, to causing said pressurized gas to be vented.

7. The system as recited in claim 6 further comprising:

flow restriction means coupled between said pressure reduction means and said safety valve means for restricting gas flow upon said pressure of said pressurized gas exceeding said safety level.

8. The system as recited in claim 1, wherein said pressurized gas feed stream includes a reactive gas.

9. The system as recited in claim 1, further comprising:

a reservoir for holding a working fluid;

first conduit means connecting said reservoir to said particle analyzer;

second conduit means having an input positioned upstream from said flow restriction means, an output coupled to a head space in said reservoir for applying said overpressure sample gas to said reservoir to pressurize said working fluid.

10. The system as recited in claim 1, wherein said flow restriction means maintains an overpressure of said gas sample in a range of from 2 to 4 pounds per square inch in excess of ambient pressure.

\* \* \* \* \*